US010529530B2

(12) United States Patent
Kawai

(10) Patent No.: US 10,529,530 B2
(45) Date of Patent: Jan. 7, 2020

(54) CHARGED PARTICLE BEAM SYSTEM

(71) Applicant: JEOL Ltd., Tokyo (JP)

(72) Inventor: Shuji Kawai, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 15/341,309

(22) Filed: Nov. 2, 2016

(65) Prior Publication Data
US 2017/0236680 A1 Aug. 17, 2017

(30) Foreign Application Priority Data

Nov. 4, 2015 (JP) .................................. 2015-216654

(51) Int. Cl.
| H01J 37/02 | (2006.01) |
| H01J 37/10 | (2006.01) |
| H01J 37/20 | (2006.01) |
| G01N 23/20091 | (2018.01) |
| H01J 37/28 | (2006.01) |

(52) U.S. Cl.
CPC ............ *H01J 37/023* (2013.01); *H01J 37/10* (2013.01); *H01J 37/20* (2013.01); *G01N 23/20091* (2013.01); *H01J 37/28* (2013.01)

(58) Field of Classification Search
None
See application file for complete search history.

(56) References Cited

U.S. PATENT DOCUMENTS

| 3,629,579 | A * | 12/1971 | Naitou | H01J 37/20 |
| | | | | 250/310 |
| 9,194,829 | B2* | 11/2015 | Smith | G01N 23/2252 |
| 2002/0050565 | A1* | 5/2002 | Tokuda | G01N 23/225 |
| | | | | 250/310 |
| 2003/0089852 | A1* | 5/2003 | Ochiai | H01J 37/256 |
| | | | | 250/310 |
| 2012/0093299 | A1* | 4/2012 | Kita | G01N 35/00732 |
| | | | | 378/208 |
| 2015/0009489 | A1* | 1/2015 | Mulders | H01J 37/261 |
| | | | | 356/72 |

(Continued)

FOREIGN PATENT DOCUMENTS

| JP | 2011153846 A | * | 8/2011 |
| JP | 2011153846 A | * | 8/2011 |

(Continued)

*Primary Examiner* — Andrew Smyth
(74) *Attorney, Agent, or Firm* — The Webb Law Firm

(57) ABSTRACT

There is provided a charged particle beam system in which a detector can be placed in an appropriate analysis position. The charged particle beam system (100) includes: a charged particle source (11) for producing charged particles; a sample holder (20) for holding a sample (S); a detector (40) for detecting, in the analysis position, a signal produced from the sample (S) by impingement of the charged particles on the sample (S); a drive mechanism (42) for moving the detector (40) into the analysis position; and a controller (52) for controlling the drive mechanism (42). The controller (52) performs the steps of: obtaining information about the type of the sample holder (20); determining the analysis position on the basis of the obtained information about the type of the sample holder (20); and controlling the drive mechanism (42) to move the detector (40) into the determined analysis position.

5 Claims, 8 Drawing Sheets

(56) References Cited

U.S. PATENT DOCUMENTS

| | | | |
|---|---|---|---|
| 2015/0221468 A1* | 8/2015 | Nomaguchi | H01J 37/265 |
| | | | 250/309 |
| 2016/0020067 A1* | 1/2016 | Iwasawa | H01J 37/244 |
| | | | 250/440.11 |
| 2017/0018397 A1* | 1/2017 | Suzuki | H01J 37/26 |

FOREIGN PATENT DOCUMENTS

| | | | | |
|---|---|---|---|---|
| JP | WO 2015145706 A1 * | 10/2015 | | H01J 37/26 |
| WO | WO 2014102733 A1 * | 7/2014 | | |
| WO | WO-2015145706 A1 * | 10/2015 | | |

* cited by examiner

CHARGED PARTICLE BEAM SYSTEM

BACKGROUND OF THE INVENTION

Field of the Invention

The present invention relates to a charged particle beam system.

Description of Related Art

Electron microscopes, such as transmission electron microscope (TEM), scanning transmission electron microscope (STEM), and scanning electron microscopes (SEM), are used as means for obtaining structural information about nano-sized materials, devices, and biological samples. Where compositional information on such samples should be obtained, an energy dispersive X-ray spectrometer (EDS) detector is equipped to such an electron microscope.

When EDS analysis is performed using an electron microscope equipped with an EDS detector, the EDS detector is inserted close to a sample placed within a sample chamber. When no EDS analysis is performed, the EDS detector is retracted from the sample chamber. By effecting such operations, where EDS analysis is not made, the electron microscope can be placed in a condition where neither observation of the sample nor exchange of the sample holder is hindered (see, for example, JP-A-2011-153846).

The insertion and retraction of the EDS detector are done under control of an EDS controller and are carried out, for example, when a user selects "IN" and "OUT", respectively, on the EDS detector via the manual control section of the EDS controller.

In an electron microscope, an electron beam is directed at a sample, and an electron microscope image is formed by detecting secondary electrons or backscattered electrons emitted from the sample, electrons transmitted through the sample, or scattering electrons. When an electron beam is made to hit a sample, there are generated characteristic X-rays attributable to materials or elements constituting the sample. The produced characteristic X-rays have different energy bands for different elements. Therefore, compositional information about the sample can be obtained by detecting the characteristic X-rays.

An EDS system including an EDS detector can detect characteristic X-rays and provide characteristic X-ray intensities which are different for different energy levels. The EDS system can perform various analyses such as point analysis, line analysis, and map analysis combined with scanned images.

In recent years, silicon drift detectors (SDDs) have been put into practical use as EDS detectors and, therefore, higher sensitivity and higher speeds of EDS analysis are being accomplished. An SDD can have an improved detection efficiency by having a larger detector active area so as to increase the detection solid angle.

The detection solid angle, $\Omega$, is given by $$\Omega = \frac{S \cdot \cos\theta}{L^2}$$

where S is the detector active area, $\theta$ is the acceptance angle, and L is the distance from the position of electron impingement on the sample to the center of the detector.

As can be seen from the above equation, in order to increase the detection solid angle of the EDS detector, the detector active area S must be increased, while the distance L must be reduced. Therefore, in order to increase the detection solid angle of the EDS detector, it is desirable to place the EDS detector as close as possible to the sample when the detector is inserted.

However, if the EDS detector is placed closer to a sample, the EDS detector and sample holder may mechanically interfere with each other. Various types of sample holders are available. Different types of sample holders have different shapes and, therefore, it is difficult to place an EDS detector in an appropriate position for analysis.

SUMMARY OF THE INVENTION

In view of the foregoing problem, the present invention has been made. One object associated with some aspects of the present invention is to provide a charged particle beam system in which a detector can be disposed in an appropriate analysis position.

(1) A charged particle beam system associated with the present invention has: a charged particle source for producing charged particles; a sample holder for holding a sample; a detector for detecting, in an analysis position, a signal produced from the sample by impingement of the charged particles on the sample; a drive mechanism for moving the detector into the analysis position; and a controller for controlling the drive mechanism. The controller performs the steps of obtaining information about the type of the sample holder, determining the analysis position on the basis of the obtained information about the type of the sample holder, and controlling the drive mechanism to move the detector into the determined analysis position.

In this charged particle beam system, the controller performs the steps as described above and so the detector can be placed in an appropriate analysis position according to the type of the sample holder. Consequently, in this charged particle beam system, the detection solid angle can be increased by reducing the distance between the detector and the sample while preventing mechanical interference between the detector and the sample holder. Hence, in this charged particle beam system, the detection efficiency of the detector can be improved.

(2) In one feature of this charged particle beam system, the sample holder may be connected with the controller via plural signal lines. The controller may obtain information about the type of the sample holder on the basis of the state of electrical connection between the signal lines.

In this charged particle beam system, the type of the sample holder can be identified with a simple structure.

(3) In another feature of the charged particle beam system of (1), the sample holder may have an information storage section in which there is stored information about the type of the sample holder. The controller may obtain the information about the type of the sample holder by reading this information about the type of the sample holder from the information storage section.

(4) In a further feature of the charged particle beam system of (1), there may be further included a manual control unit permitting a user to enter information about the type of the sample holder. The controller may obtain the information about the type of the sample holder on the basis of the information about the type of the sample holder entered via the manual control unit.

In this charged particle beam system, information about the type of the sample holder can be obtained without the need to interconnect the sample holder and the controller, for example, by a signal line such as a communication cable.

(5) In one feature of the charged particle beam system of any one of (1)-(4), there may be further included an objective lens. The controller may perform the step of obtaining information about the type of the objective lens. During the step of determining the analysis position, the controller may determine the analysis position on the basis of both the information about the type of the sample holder and the information about the type of the objective lens.

In this charged particle beam system, the controller performs the steps as described above and so the detector can be disposed in an appropriate analysis position according both to the type of the sample holder and to the type of the objective lens. Therefore, in this charged particle beam system, the detection solid angle can be increased by reducing the distance between the detector and the sample while preventing both mechanical interference between the detector and the sample holder and the mechanical interference between the detector and the objective lens.

DESCRIPTION OF THE INVENTION

The preferred embodiments of the present invention are hereinafter described in detail with reference to the drawings. It is to be understood that the embodiments described below are not intended to unduly restrict the content of the present invention delineated by the claims and that not all the configurations described below are essential constituent components of the invention.

1. First Embodiment 1.1. Charged Particle Beam System

Figure 1:
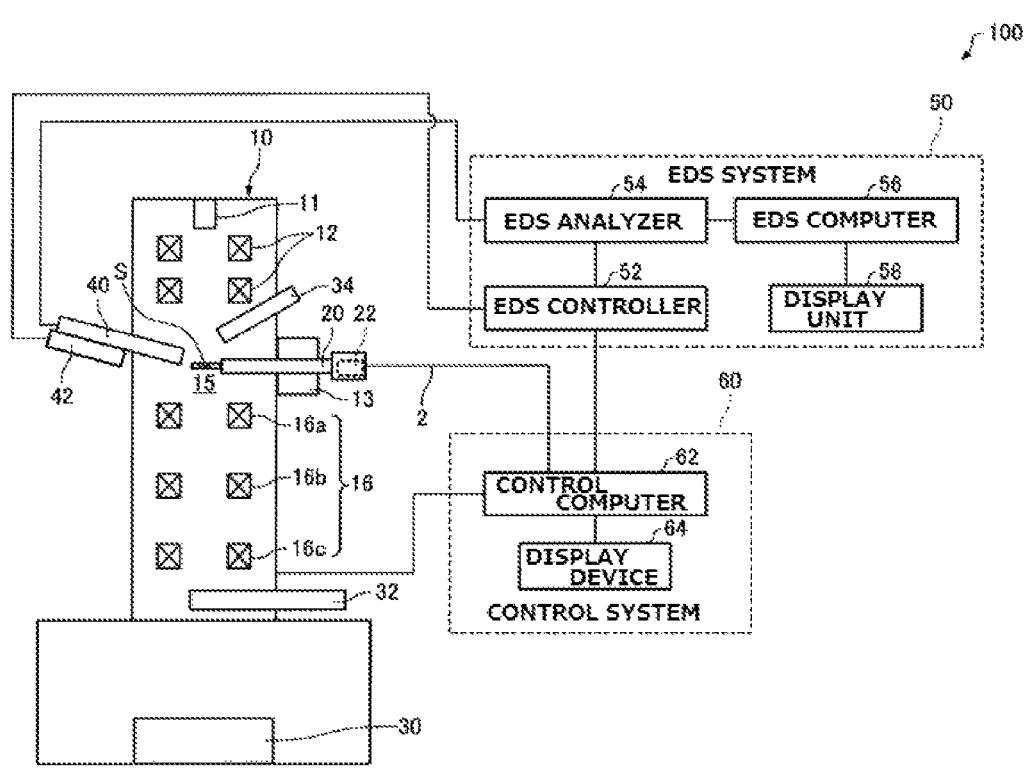
FIG. 1 is a schematic representation, partly in block form, of a charged particle beam system associated with a first embodiment of the present invention.

A charged particle beam system associated with a first embodiment of the present invention is first described by referring to FIG. 1, which schematically shows the charged particle beam system, generally indicated by reference numeral 100.

As shown in FIG. 1, the charged particle beam system 100 whose body portion is indicated by numeral 10 includes a sample holder 20, an image capture device 30, an STEM detector 32, a secondary electron detector 34, an EDS detector 40, a drive mechanism 42, an EDS system 50, and a control system 60.

The body portion 10 of the charged particle beam system includes an electron source 11 (which is one example of a charged particle source), an illumination lens system 12, a sample stage 13, and an imaging lens system 16.

The electron source 11 produces electrons which are one kind of charged particles. For example, the electron source 11 is an electron gun that emits an electron beam by accelerating electrons, emitted from a cathode, by means of an anode.

The electron beam generated by the electron source 11 is focused onto a sample S by the illumination lens system 12 in a sample chamber 15 such that the beam impinges on the sample S.

The charged particle beam system 100 may be configured including deflectors (not shown) for causing the electron beam (electron probe) focused by the illumination lens system 12 to be scanned over the sample S.

The sample stage 13 holds the sample S via the sample holder 20. The sample stage 13 can move and stop the sample holder 20 (and the sample S). The sample stage 13 can place the sample S in position.

The sample chamber 15 is a space where the sample S is placed. In the sample chamber 15, electrons are made to impinge on the sample S. The interior of the sample chamber 15 is vacuum pumped by vacuum pumping equipment (not shown).

The imaging lens system 16 forms an image from electrons transmitted through the sample S. The imaging lens system 16 is made up of an objective lens 16a, an intermediate lens 16b, and a projector lens 16c.

The sample holder 20 holds the sample S. The sample stage 13 has a receptacle portion in which the sample holder 20 holding the sample S is inserted. Thus, the sample S is accommodated in the sample chamber 15. FIG. 1 shows a state in which the sample holder 20 has been inserted in the sample chamber 15.

The sample holder 20 is connected to a control computer 62 and to an EDS controller 52 via communication cabling 2. In the illustrated example, the sample holder 20 is connected to the EDS controller 52 via both communication cabling 2 and control computer 62. Alternatively, the sample holder 20 and EDS controller 52 may be interconnected by a communication cable without via the control computer 62 in an unillustrated manner.

The communication cabling 2 is used for communications between the sample holder 20 and the EDS controller 52 through the control computer 62. The communication cabling 2 is ancillary to the sample holder 20, and connected to the control computer 62 via a connector. The communication cabling 2 has a plurality of signal lines.

In the communication route between the sample holder 20 and the EDS controller 52 via the control computer 62, there may be A/D converters (not shown) or other circuits for converting signals output from the sample holder 20 into a form that is readable by the control computer 62 and EDS controller 52.

The sample holder 20 has a type identification portion 22 for identification of the type of the sample holder 20. The type identification portion 22 will be described in detail later. The sample holder 20 may have a tilt stage for tilting the sample S, a rotary stage for rotating the sample S, a heater for controlling the temperature of the sample S, and other means. Control signals for controlling the tilting stage and other devices may be sent to the sample holder 20 from the control computer 62 via the communication cabling 2.

The image capture device 30 obtains a TEM (transmission electron microscope) image focused by the imaging lens system 16, for example, using a digital camera such as a CCD camera or CMOS camera.

The STEM detector 32 detects the intensity of transmitted wave or diffracted wave passing through each point on the sample S by scanning the electron probe over the sample S. The output signal from the STEM detector 32 is stored as STEM image data in a storage section (not shown) while being associated with information about the positions of electron impingement.

The secondary electron detector 34 detects secondary electrons emitted from each point on the sample S in response to scanning of the electron probe over the sample S. The output signal from the secondary electron detector 34 is stored as SE (secondary electron) image data into the storage section (not shown) while being associated with information about the positions of electron impingement.

The EDS detector 40 detects characteristic X-rays (which are one example of signal produced from the sample by impingement of charged particles on the sample) emanating from the sample S in response to impingement of electrons on the sample S. For example, the EDS detector 40 is a silicon drift detector.

An analysis position at which the EDS detector 40 detects the characteristic X-rays emanating from the sample S is located within the sample chamber 15 and close to the sample S. The analysis position of the EDS detector 40 is determined by the EDS controller 52 based on information about the type of the sample holder 20 as described later.

The drive mechanism 42 moves the EDS detector 40 into the analysis position. The drive mechanism 42 operates to insert the detector 40 into the analysis position within the sample chamber 15 and to retract the detector 40 from inside the sample chamber 15.

The drive mechanism 42 is configured, for example, including a guide portion and a linear actuator for moving the EDS detector 40 on the guide portion on which the EDS detector 40 is slidably mounted. Position sensors are mounted on the guide portion to detect the position of the EDS detector 40. The plural position sensors are mounted in a corresponding manner to the plural analysis positions of the EDS detector 40. When the EDS detector 40 is located in the detection position of any one of the position sensors, this position sensor provides a detection signal. Note that no restriction is imposed on the configuration of the drive mechanism 42 as long as it can insert and retract the detector.

The EDS system 50 is used to perform EDS analysis. The EDS system 50 has the above-described EDS controller 52 (that is one example of controller), an EDS analyzer 54, an EDS computer 56, and a display unit 58.

The EDS controller 52 controls the drive mechanism 42. The processing performed by the EDS controller 52 will be described later in "1.2. Operation of Charged Particle Beam System". The functions of the EDS controller 52 may be implemented by executing computer programs by means of a processor (such as a CPU or a DSP) or by using dedicated circuitry such as an ASIC (e.g., a gate array).

The EDS analyzer 54 is a multichannel pulse height analyzer having multiple channels. The EDS analyzer 54 counts the output signal from the EDS detector 40 for each X-ray energy range.

The EDS computer 56 generates an EDS spectrum based on counts obtained by the EDS analyzer 54 for each X-ray energy range.

The display unit 58 is an LCD, CRT, or the like. The EDS spectrum generated by the EDS computer 56 is displayed on the display unit 58.

The control system 60 controls the body portion 10 of the charged particle beam system, as well as the components and devices making up the charged particle beam system 100 such as the sample holder 20. The control system 60 has the control computer 62 and a display device 64.

The control computer 62 performs processing to control the body portion 10 of the charged particle beam, the sample holder 20, and other components.

The display device 64 is an LCD, CRT, or the like. Information about various operating parameters such as the position of the sample holder 20, tilt angle, imaging mode (e.g., TEM mode, STEM mode, or SEM mode), and final magnification is displayed on the display device 64.

As noted previously, the charged particle beam system 100 functions as transmission electron microscope (TEM), scanning transmission electron microscope (STEM), and scanning electron microscope (SEM). Note that the charged particle beam system 100 may function as at least one of transmission electron microscope (TEM), scanning transmission electron microscope (STEM), and scanning electron microscope (SEM).

Figure 2:
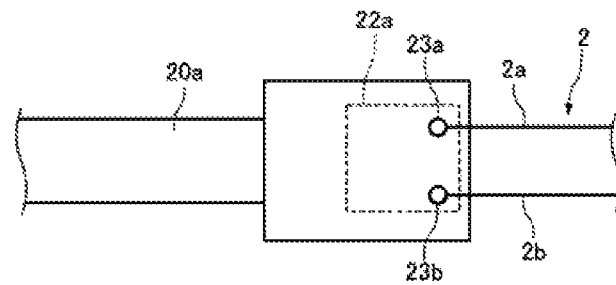
FIG. 2 is a schematic representation of a normal type sample holder identification portion.
Figure 3:
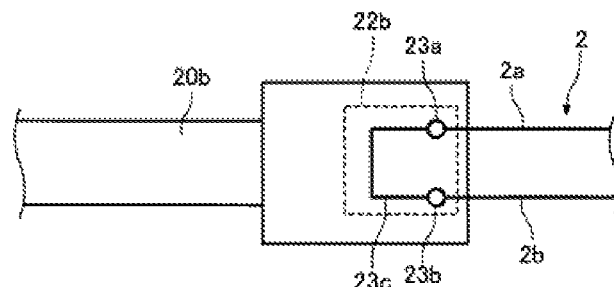
FIG. 3 is a schematic representation of a large solid angle compliant type sample holder identification portion.

The type identification portion 22 for identification of the type of the sample holder 20 is next described. FIG. 2 schematically shows a type identification portion 22a for a normal type sample holder 20a that is one type of the sample holder 20. FIG. 3 schematically shows a type identification portion 22b for a large solid angle compliant type sample holder 20b that is another type of the sample holder 20. Each of FIGS. 2 and 3 shows a state in which the communication cabling 2 is connected to the sample holder 20a or 20b, respectively.

Figure 6:
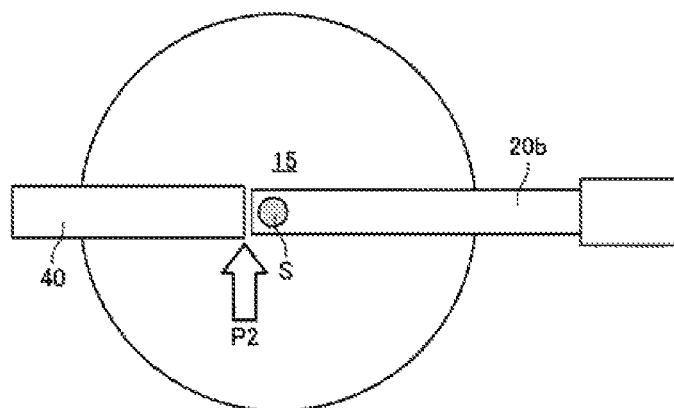
FIG. 6 illustrates an analysis position of the EDS detector assumed when the large solid angle compliant type sample holder has been inserted.

The sample holder of the large solid angle compliant type referred to herein is designed to be capable of increasing the detection solid angle by placing the EDS detector 40 closer to the sample S than achievable by the sample holder of the normal type. For example, the sample holder 20b of the large solid angle compliant type has a shortened front end portion as shown in FIG. 6. The shortened front end portion permits the EDS detector 40 to be placed closer to the sample S.

As shown in FIG. 2, the type identification portion 22a for the normal type sample holder 20a has a first terminal 23a and a second terminal 23b. When the communication cabling 2 is connected with the sample holder 20a, the first terminal 23a is connected with a first signal line 2a of the communication cabling 2, while the second terminal 23b is connected with the second signal line 2b of the communication cabling 2. In the type identification portion 22a, no electrical connection is made between the first terminal 23a and the second terminal 23b. Therefore, when the communication cabling 2 has been connected with the sample holder 20a, there is no electrical connection between the first signal line 2a and the second signal line 2b. That is, when the communication cabling 2 is connected with the sample holder 20a, the electrical connection between the signal lines 2a and 2b is open.

As shown in FIG. 3, the type identification portion 22b for the sample holder 20b of the large solid angle compliant type has a first terminal 23a and a second terminal 23b in the same way as the type identification portion 22a. In the type identification portion 22b, the first terminal 23a and the second terminal 23b are electrically interconnected by a lead wire 23c. Therefore, when the communication cabling 2 is connected with the sample holder 20b, the first signal line 2a and second signal line 2b are electrically interconnected. That is, when the communication cabling 2 is connected to the sample holder 20b, the electrical connection between the signal lines 2a and 2b is closed.

1.2. Operation of Charged Particle Beam System

Figure 4:
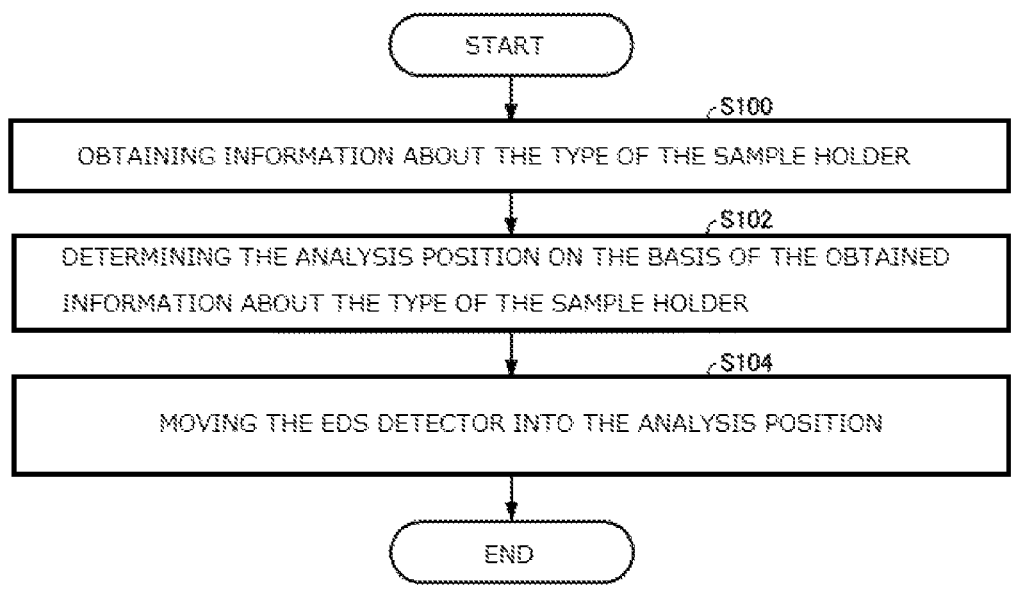
FIG. 4 is a flowchart illustrating one example of processing subroutine performed by an EDS controller of the system of FIG. 1.

The operation of the charged particle beam system 100 is next described. An insertion operation in which the EDS detector 40 is moved into an analysis position is now described. FIG. 4 is a flowchart illustrating one example of processing subroutine performed by the EDS controller 52.

First, the EDS controller 52 obtains information about the type of the sample holder 20 (step S100). The information about the type of the sample holder 20 that the EDS controller 52 obtains is used to identify the type of the sample holder 20 now inserted in the sample chamber 15.

The EDS controller 52 obtains information about the type of the sample holder 20 on the basis of the state of electrical connection between the first signal line 2a and the second signal line 2b. In particular, when the electrical connection between the signal lines 2a and 2b is open (see FIG. 2), the EDS controller 52 identifies the currently inserted sample holder 20 as the sample holder 20a of the normal type. When the electrical connection between the signal lines 2a and 2b is closed (see FIG. 3), the EDS controller 52 identifies the presently inserted sample holder 20 as the sample holder 20b of the large solid angle compliant type.

Then, the EDS controller 52 determines the analysis position of the EDS detector 40 on the basis of the obtained information about the type of the sample holder 20 (step S102).

Figure 5:
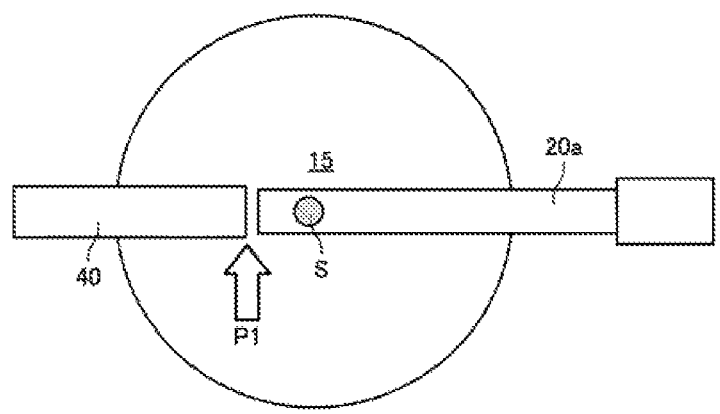
FIG. 5 illustrates an analysis position of an EDS detector of the system of FIG. 1 assumed when the normal type sample holder has been inserted.

FIG. 5 shows an analysis position P1 of the EDS detector 40 assumed when the sample holder 20a of the normal type has been inserted. FIG. 6 shows an analysis position P2 of the EDS detector 40 assumed when the sample holder 20b of the large solid angle compliant type has been inserted. FIGS. 5 and 6 show states in which the EDS detector 40 is located in analysis positions.

When the presently inserted sample holder 20 is the sample holder 20a of the normal type, the EDS controller 52 determines the analysis position P1 (FIG. 5) as the analysis position of the EDS detector 40.

When the currently inserted sample holder 20 is the sample holder 20b of the large solid angle compliant type, the EDS controller 52 determines the analysis position P2 (FIG. 6) as the analysis position of the EDS detector 40. The analysis position P2 is closer to the sample S than the analysis position P1.

The EDS controller 52 has a storage unit (not shown) in which there is stored information about analysis positions of the EDS detector 40 according to the types of the sample holder 20. The EDS controller 52 determines the analysis position of the EDS detector 40 by matching the obtained information about the type of the sample holder 20 against the information stored in the storage unit. Information about the determined analysis position of the EDS detector 40 is stored in the storage unit of the EDS controller 52.

The EDS controller 52 then controls the drive mechanism 42 to move the EDS detector 40 into the analysis position determined in step S102 (step S104).

If a user or an automatic sequence of commands issues an instruction to insert the EDS detector 40, the EDS controller 52 performs a control operation to move the EDS detector 40 into the analysis position. In particular, the EDS controller 52 reads information about an analysis position from the storage unit and moves the EDS detector 40 into this analysis position in response to the detection signal emanating from the position sensor of the drive mechanism 42. Because of the processing sequence described so far, the EDS detector 40 can be moved into the analysis position complying with the type of the sample holder 20.

The charged particle beam system 100 has the following features. In the charged particle beam system 100, the EDS controller 52 performs the step S100 of obtaining information about the type of the sample holder 20, the step S102 of determining an analysis position on the basis of the obtained information about the type of the sample holder 20, and the step S104 of controlling the drive mechanism 42 to move the EDS detector 40 into the determined analysis position.

Consequently, in the charged particle beam system 100, the EDS detector 40 can be placed in an appropriate analysis position according to the type of the sample holder 20. Thus, in the charged particle beam system 100, the detection solid angle can be increased by reducing the distance between the EDS detector 40 and the sample S while preventing mechanical interference between the EDS detector 40 and the sample holder 20. Hence, in the charged particle beam system 100, the detection efficiency of the EDS detector 40 can be improved.

In the charged particle beam system 100, the EDS controller 52 obtains information about the type of the sample holder 20 on the basis of the state of electrical connection between the plural signal lines 2a and 2b. Therefore, in the charged particle beam system 100, the type of the sample holder 20 can be identified with a simple structure.

1.3. Modifications of Charged Particle Beam System

Modifications of the charged particle beam system 100 associated with the first embodiment are next described. In the following modifications, those members which have the same functions as their respective counterparts of the above-described charged particle beam system 100 are indicated by the same reference numerals as in the above referenced figures and a detailed description thereof is omitted.

(1) First Modification

Figure 7:
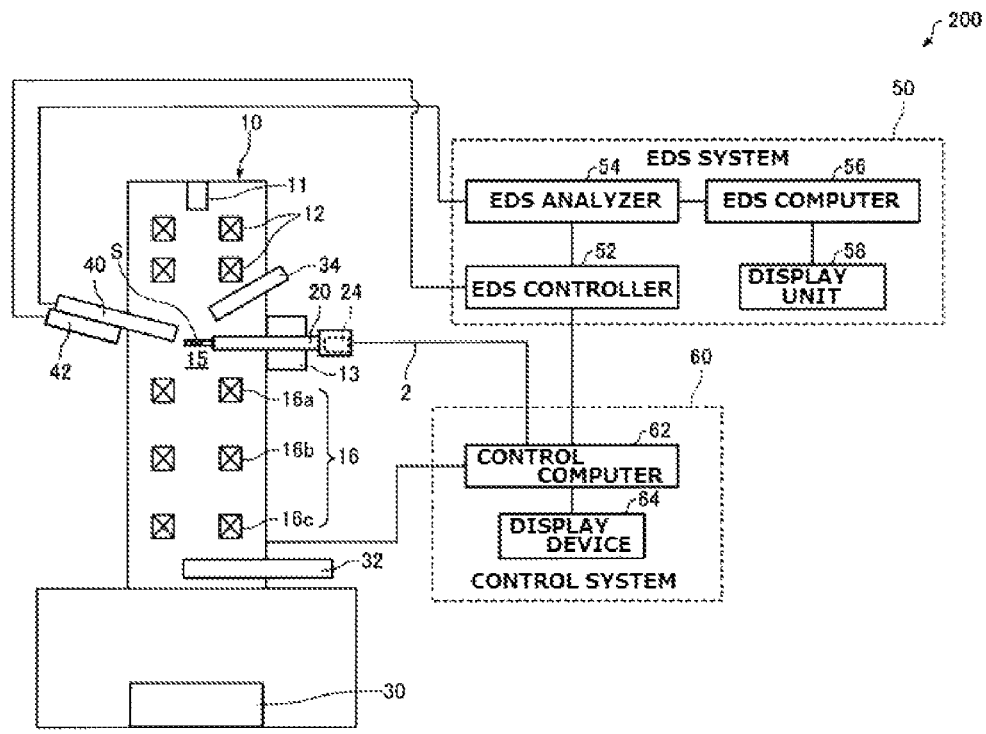
FIG. 7 is a schematic representation, partly in block form, of a charged particle beam system associated with a first modification of the first embodiment.

A charged particle beam system associated with a first modification of the first embodiment is first described by referring to FIG. 7, which schematically shows the charged particle beam system, 200, associated with the first modification.

In the above-described charged particle beam system 100, the EDS controller 52 obtains information about the type of the sample holder 20 on the basis of the state of electrical connection between the plural signal lines 2a and 2b as shown in FIGS. 3 and 4.

On the other hand, in the charged particle beam system 200, as shown in FIG. 7, the EDS controller 52 reads information about the type of the sample holder 20 from the storage unit 24 of the sample holder 20 and obtains the information about the type of the sample holder 20.

The sample holder 20 has the storage section 24 in which information about the type of the sample holder 20 is stored. The storage section 24 is a storage medium such as a ROM.

The EDS controller 52 reads information about the type of the sample holder 20 from the storage section 24 via both communication cabling 2 and control computer 62. Alternatively, the sample holder 20 and the EDS controller 52 may be interconnected by a communication cable without via the control computer 62 in an unillustrated manner such that the EDS controller 52 may directly read information about the type of the sample holder 20 from the storage section 24.

The charged particle beam system 200 is similar in operation to the charged particle beam system 100 except for the operation (step S100) in which the EDS controller 52 obtains information about the type of the sample holder 20 as described previously and so a description of the operation of the charged particle beam system 200 is omitted.

In the charged particle beam system 200, the EDS controller 52 reads information about the type of the sample holder 20 from the storage section 24 of the sample holder 20 and obtains the information about the type of the sample holder 20. Therefore, in the charged particle beam system 200, the EDS detector 40 can be placed in an appropriate analysis position according to the type of the sample holder 20 in the same way as in the charged particle beam system 100.

(2) Second Modification

Figure 8:
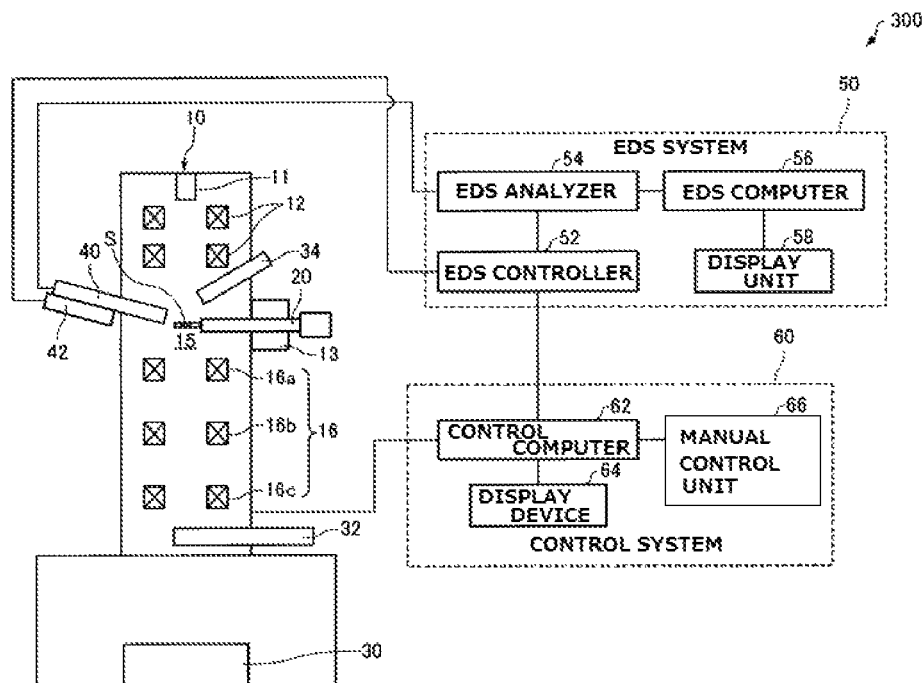
FIG. 8 is a schematic representation, partly in block form, of a charged particle beam system associated with a second modification of the first embodiment.

A charged particle beam system associated with a second modification of the first embodiment is next described by referring to FIG. 8, which schematically shows the charged particle beam system, 300, associated with the second modification.

Those members of the charged particle beam system 300 which are similar in function to their respective counterparts of the above-described charged particle beam system 100 are indicated by the same reference numerals as in the above referenced figures and a detailed description thereof is omitted.

In the above-described charged particle beam system 100, the EDS controller 52 obtains information about the type of the sample holder 20 on the basis of the state of electrical connection between the plural signal lines 2a and 2b as shown in FIGS. 3 and 4.

On the other hand, in the charged particle beam system 300, as shown in FIG. 8, the EDS controller 52 obtains information about the type of the sample holder 20 on the basis of information about the type of the sample holder 20 entered via a manual control unit 66.

The control system 60 has the manual control unit 66 permitting a user to enter information about the type of the sample holder 20. The manual control unit 66 operates to obtain a control signal responsive to a user's manipulation and to send the signal to the control computer 62. The manual control unit 66 is made of buttons, keys, a touch panel display, a microphone, or the like.

The control computer 62 performs processing to send the information about the type of the sample holder 20, which has been entered via the manual control unit 66, to the EDS controller 52. The EDS controller 52 receives the information about the type of the sample holder 20 from the control computer 62 and obtains the information about the type of the holder 20.

The charged particle beam system 300 is similar in operation to the charged particle beam system 100 except for the operation (step S100) in which the EDS controller 52 obtains information about the type of the sample holder 20 as described previously and so a description of the operation of the system 300 is omitted.

In the charged particle beam system 300, the EDS controller 52 obtains information about the type of the sample holder 20 on the basis of information about the type of the sample holder 20 entered via the manual control unit 66. Therefore, in the charged particle beam system 300, the EDS detector 40 can be placed in an appropriate analysis position according to the type of the sample holder 20 in the same way as in the charged particle beam system 100.

Furthermore, in the charged particle beam system 300, information about the type of the sample holder 20 can be derived without the need to interconnect the sample holder 20 and the control computer 62 by communication cabling such as the communication cabling 2 used in the charged particle beam system 100.

(3) Third Modification

Figure 9:
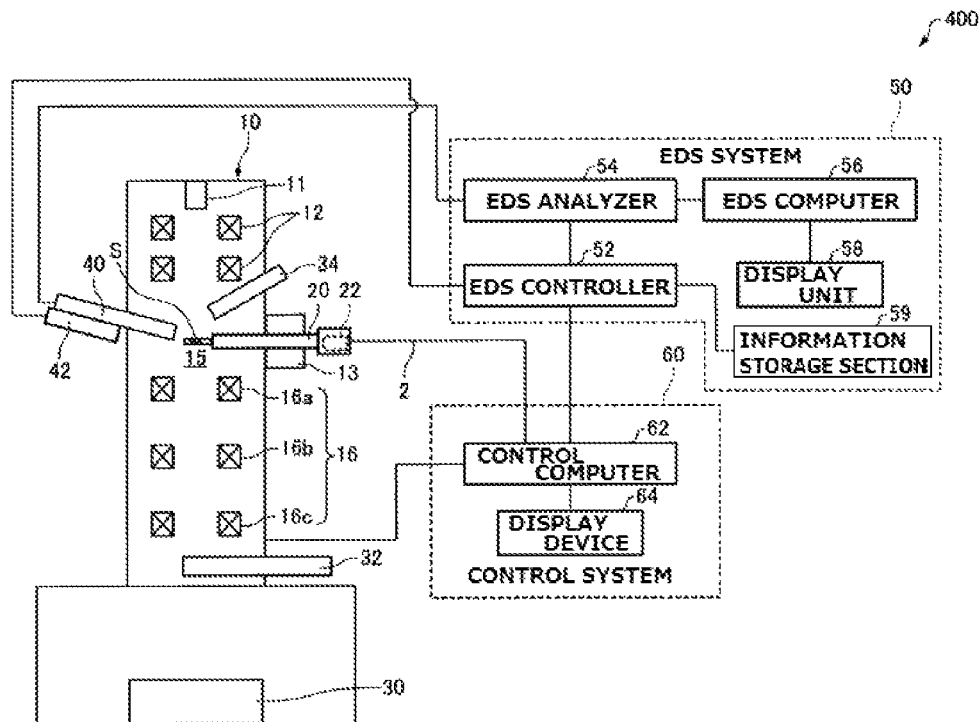
FIG. 9 is a schematic representation, partly in block form, of a charged particle beam system associated with a third modification of the first embodiment.

A charged particle beam system associated with a third modification of the first embodiment is next described by referring to FIG. 9, which schematically shows the charged particle beam system, 400, associated with the third modification.

In the above-described charged particle beam system 100, the EDS controller 52 determines the analysis position of the EDS detector 40 on the basis of information about the type of the sample holder 20.

In contrast, in the charged particle beam system 400, the EDS controller 52 determines the analysis position of the EDS detector 40 on the basis of both information about the type of the sample holder 20 and information about the type of the objective lens 16a, for the reason described below.

Figure 10:
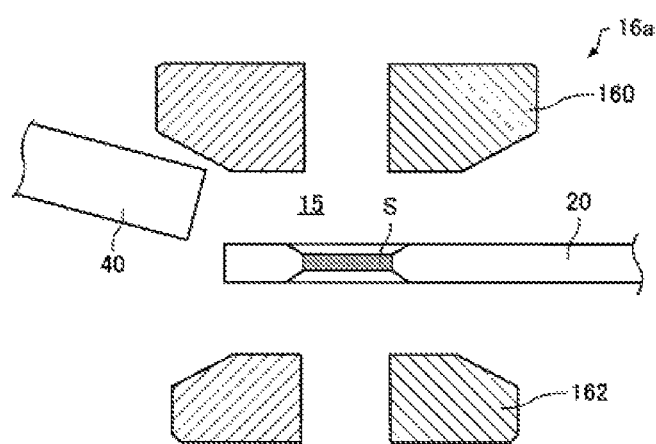
FIG. 10 is a schematic representation of a sample chamber in the charged particle beam system of FIG. 9.

FIG. 10 schematically shows the sample chamber 15 of the charged particle beam system 400. FIG. 10 shows a state in which the sample holder 20 has been inserted in the sample chamber 15 and the EDS detector 40 is located in an analysis position.

As shown in FIG. 10, the objective lens 16a has a top polepiece 160 and a bottom polepiece 162. A sample S held in the sample holder 20 is disposed in the space between the top polepiece 160 and bottom polepiece 162. Therefore, in order to prevent mechanical interference between the EDS detector 40 and the objective lens 16a, the type of the objective lens 16a must be taken into account in addition to the type of the sample holder 20 in determining the analysis position of the EDS detector 40.

Accordingly, in the charged particle beam system 400, the EDS controller 52 determines the analysis position of the EDS detector 40 on the basis of both information about the type of the sample holder 20 and information about the type of the objective lens 16a.

As shown in FIG. 9, the EDS system 50 has an information storage section 59, which stores information about the analysis position of the EDS detector 40 according to both the type of the sample holder 20 and the type of the objective lens 16a. The information storage section 59 is a storage device such as a ROM or a hard disk.

Table 1 below illustrates analysis positions of the EDS detector 40 according to types of the sample holder 20 and to types of the objective lens 16a.

TABLE 1

|  | sample holder of normal type | | sample holder of large solid angle compliant type | |
| --- | --- | --- | --- | --- |
| objective lens | A | B | A | B |
| analysis position | P1 | P3 | P2 | P4 |

In this table, A and B indicate types of the objective lens 16*a*. For example, objective lens A has normal polepieces. Objective lens B has polepieces adapted for high resolution. P1-P4 indicate analysis positions of the EDS detector 40.

Use of Table 1 makes it possible to determine the analysis position of the EDS detector 40 from both the type of the sample holder 20 and the type of the objective lens 16*a*.

Figure 11:
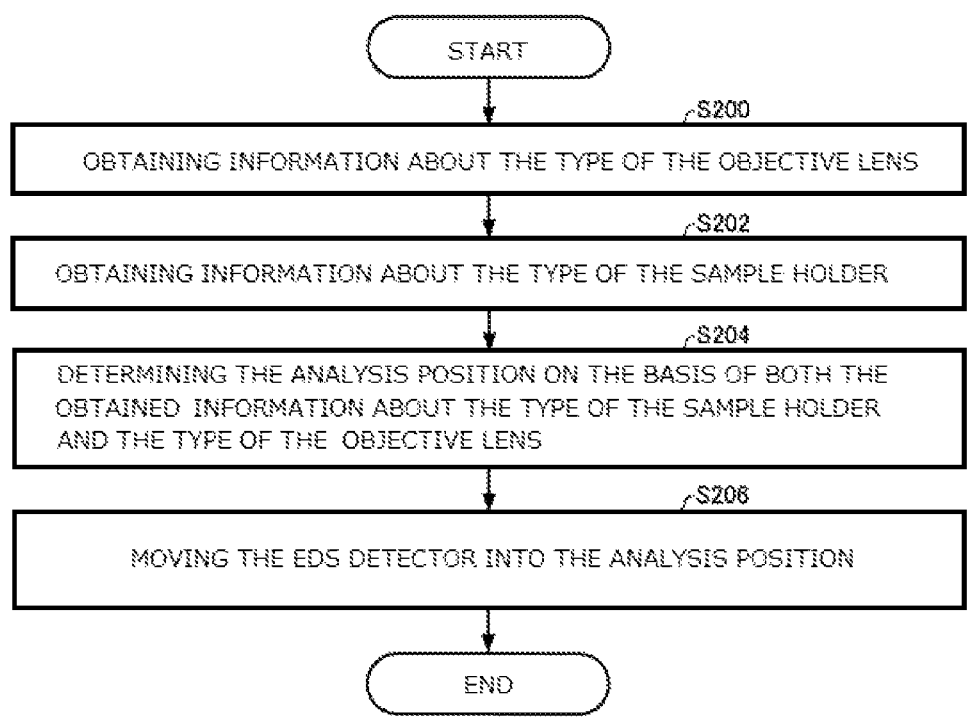
FIG. 11 is a flowchart illustrating one example of processing subroutine performed by an EDS controller included in the charged particle beam system of FIG. 9.

The operation of the charged particle beam system 400 is next described. FIG. 11 is a flowchart illustrating one example of processing subroutine performed by the EDS controller 52 of the charged particle beam system 400.

First, the EDS controller 52 obtains information about the type of the objective lens 16*a* (step S200).

The EDS controller 52 obtains information about the type of the objective lens 16*a* from the control computer 62. The control computer 62 performs processing to send the information about the type of the objective lens 16*a*, which has been entered by the user via the manual control unit (not shown), to the EDS controller 52. The EDS controller 52 receives the information about the type of the objective lens 16*a* from the control computer 62 and obtains the information about the type of the objective lens 16*a* now in use.

Then, the EDS controller 52 obtains information about the type of the sample holder 20 (step S202). Since step S202 is identical to the above-described step S100, a description thereof is omitted.

The EDS controller 52 then determines the analysis position of the EDS detector 40 on the basis of both the obtained information about the type of the sample holder 20 and the obtained information about the type of the objective lens 16*a* (step S204).

The EDS controller 52 then matches the obtained information about the type of the sample holder 20 and the obtained information about the type of the objective lens 16*a* against information about analysis positions of the EDS detector 40 (see Table 1) corresponding to the types of the sample holder 20 and types of the objective lens 16*a* stored in the storage section 59, and determines the analysis position of the EDS detector 40. Information about the determined analysis position of the EDS detector 40 is stored in the storage section of the EDS controller 52.

The EDS controller 52 then controls the drive mechanism 42 to move the EDS detector 40 into the analysis position determined at step S204 (step S206). Since step S206 is identical to the above-described step S104, a description thereof is omitted.

Because of the processing subroutine described so far, the EDS detector 40 can be moved into an analysis position according to both the type of the sample holder 20 and the type of the objective lens 16*a*.

In the charged particle beam system 400, during the process (step S204) of determining the analysis position of the EDS detector 40, the EDS controller 52 determines the analysis position of the EDS detector 40 on the basis of both information about the type of the sample holder 20 and information about the type of the objective lens 16*a*. Therefore, in the charged particle beam system 400, the EDS detector 40 can be placed in an appropriate analysis position according to both the type of the sample holder 20 and the type of the objective lens 16*a*. Consequently, in the charged particle beam system 400, the detection solid angle can be increased by reducing the distance between the EDS detector 40 and the sample S while preventing mechanical interference between the EDS detector 40 and the sample holder 20 and mechanical interference between the EDS detector 40 and the objective lens 16*a*.

(4) Fourth Modification

A charged particle beam system associated with a fourth modification of the first embodiment is next described. The charged particle beam system associated with the fourth modification is identical in configuration to the charged particle beam system 100 shown in FIG. 1 and thus is omitted from being shown. Only the differences with the above-described charged particle beam system 100 are described below; a description of similarities is omitted.

In the charged particle beam system associated with the fourth modification, if the EDS controller 52 cannot make communications with the sample holder 20, the EDS controller 52 brings the analysis position of the EDS detector 40 into a position where there occurs no mechanical interference at all with whatever type of sample holder 20.

Some types of sample holders are not connected to the control computer 62 by the communication cabling 2. One example of such sample holders is equipped with none of tilting stage, rotary stage, heater, and so on because this example of sample holder does not need to perform communications with the control system 60.

Furthermore, some types of sample holders are not compliant with EDS analysis. One example is a sample holder which is not coated with a beryllium material and thus cannot be easily detected with an EDS detector.

If such a sample holder has been inserted, the EDS detector 40 would not normally be inserted into the sample chamber 15. However, due to a user's operational error or for other reason, the EDS detector 40 may be inserted into the sample chamber 15. In preparation for such circumstances, if no communications can be made with the sample holder 20, the EDS controller 52 brings the analysis position of the EDS detector 40 into a position where no mechanical interference occurs with whatever type of sample holder 20 as described previously.

2. Second Embodiment

Figure 12:
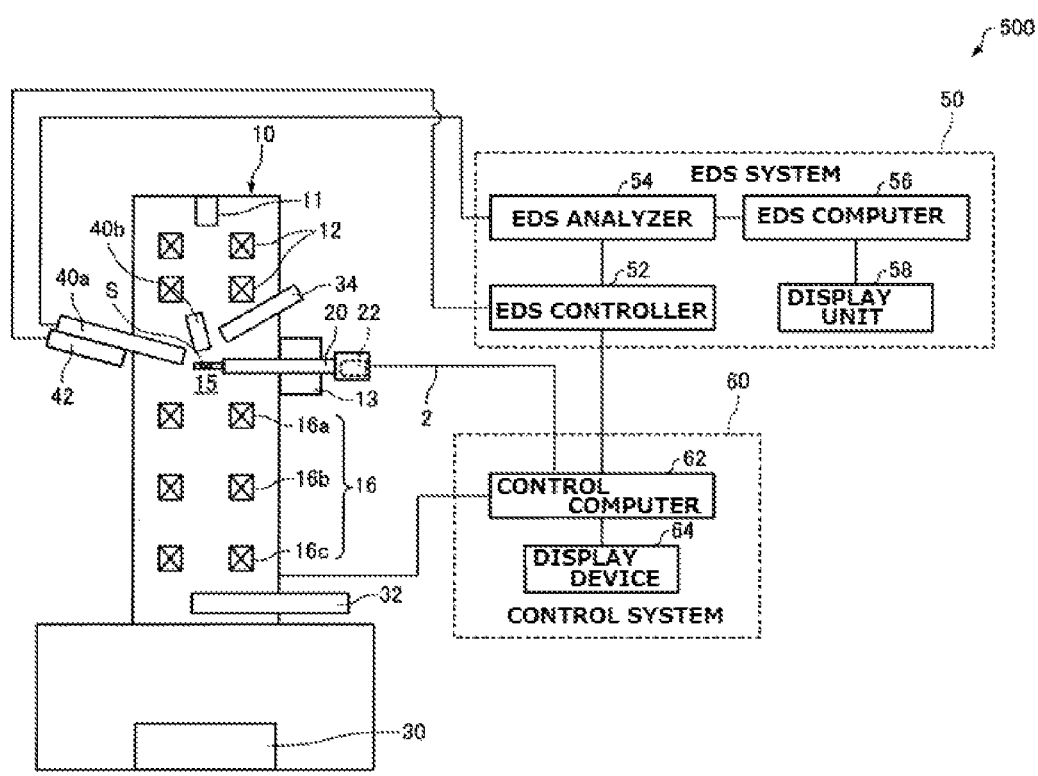
FIG. 12 is a schematic representation, partly in block form, of a charged particle beam system associated with a second embodiment.
Figure 13:
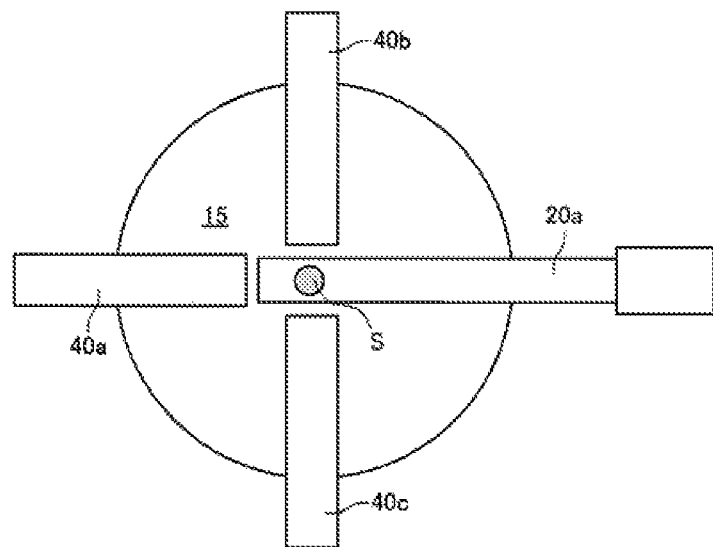
FIG. 13 illustrates an analysis position of an EDS detector of the system of FIG. 12 assumed when the normal type sample holder has been inserted.
Figure 14:
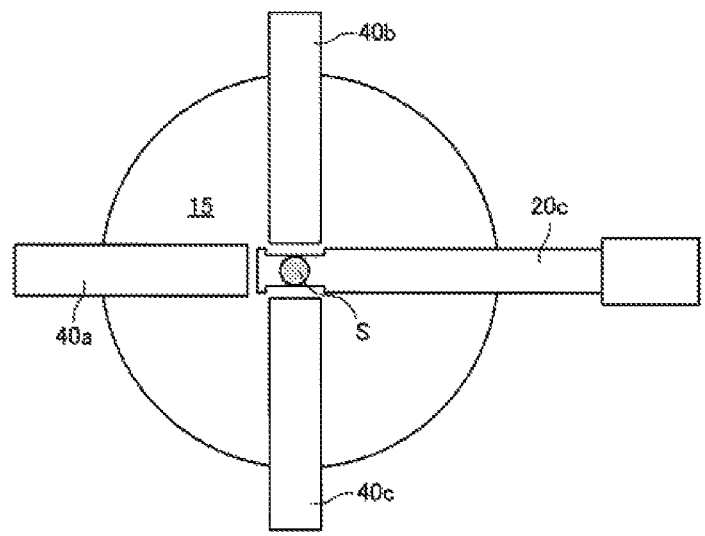
FIG. 14 illustrates an analysis position of the EDS detector assumed when the large solid angle compliant type sample holder has been inserted.

A charged particle beam system associated with a second embodiment is next described by referring to some drawings. FIG. 12 schematically shows the charged particle beam system, 500, associated with the second embodiment. FIG. 13 shows analysis positions of EDS detectors 40*a*, 40*b*, and 40*c* assumed when a sample holder 20*a* of the normal type has been inserted. FIG. 14 shows analysis positions of the EDS detectors 40*a*, 40*b*, and 40*c* assumed when a sample holder 20*c* of the large solid angle compliant type has been inserted. FIGS. 13 and 14 show states in which the EDS detectors 40*a*, 40*b*, and 40*c* are in their analysis positions.

Those members of the charged particle beam system 500 associated with the second embodiment which are similar in function to their respective counterparts of the charged particle beam system 100 associated with the first embodiment are indicated by the same reference numerals as in the above referenced figures and a detailed description thereof is omitted.

As shown in FIGS. 12-14, the charged particle beam system 500 has a plurality of EDS detectors 40 (i.e., 40*a*-40*c*). In the illustrated example, the charged particle beam system 500 has three EDS detectors, i.e., first EDS detector 40*a*, second EDS detector 40*b*, and third EDS detector 40*c*. Furthermore, the system 500 includes a drive mechanism 42 for moving the first EDS detector 40*a*, another drive mechanism (not shown) for moving the second EDS detector 40*b*, and a further drive mechanism (not shown) for moving the third EDS detector 40*c*. Note that no restriction is imposed on the number of EDS detectors in the charged particle beam system 500.

Since the charged particle beam system 500 has the plural EDS detectors 40a, 40b, and 40c, improved detection sensitivity can be provided. As shown in FIGS. 13 and 14, the EDS detectors 40a, 40b, and 40c are disposed in different directions.

The sample holder 20c of the large solid angle compliant type shown in FIG. 14 has a front end portion which has length and width that are smaller than those of the normal type sample holder 20a of FIG. 13. Consequently, with the sample holder 20c of the large solid angle compliant type, the EDS detectors 40a, 40b, and 40c can be placed closer to the sample S than the normal type sample holder 20a.

The EDS controller 52 of the charged particle beam system 500 is similar in operation to the EDS controller 52 of the above-described charged particle beam system 100 except that steps S102 and S104 are performed for each of the EDS detectors 40a, 40b, and 40c and so a description of the operation of the EDS controller 52 is omitted.

In the charged particle beam system 500, the plural EDS detectors 40a, 40b, and 40c can be placed in appropriate analysis positions according to the type of the sample holder 20 in the same way as in the above-described charged particle beam system 100.

The above-described first through fourth modifications of the first embodiment are similarly applicable to the charged particle beam system 500 associated with the second embodiment.

3. Other Embodiments

It is to be understood that the present invention is not restricted to the above-described embodiments and that they can be practiced in variously modified forms within the gist of the present invention.

For example, in the above embodiments, examples are given in which the charged particle beam system functions as a transmission electron microscope, a scanning transmission electron microscope, and a scanning electron microscope. The charged particle beam system associated with the present invention may be an instrument in which a sample can be irradiated with charged particles such as electrons or ions for observation, analysis, or machining. The charged particle beam system associated with the present invention may also be an electron probe microanalyzer (EPMA), a focused ion beam system, or the like.

It is to be understood that the above embodiments and modifications are merely exemplary and that the invention is not restricted thereto. For example, the embodiments and modifications can be appropriately combined.

The present invention embraces configurations substantially identical (e.g., in function, method, and results or in purpose and advantageous effects) with the configurations described in any one of the embodiments of the invention. Furthermore, the invention embraces configurations described in the embodiments and including portions which have non-essential portions replaced. In addition, the invention embraces configurations which produce the same advantageous effects as those produced by the configurations described in the embodiments or which can achieve the same objects as the configurations described in the embodiments. Further, the invention embraces configurations which are similar to the configurations described in the embodiments except that well-known techniques have been added.

Having thus described my invention with the detail and particularity required by the Patent Laws, what is desired protected by Letters Patent is set forth in the following claims.

The invention claimed is:

1. A charged particle beam system comprising:
a charged particle source for producing charged particles;
a sample holder for holding a sample;
a detector for detecting, in an analysis position, a signal produced from the sample by impingement of the charged particles on the sample;
a drive mechanism for moving the detector into a plurality of analysis positions; and
a controller for controlling the drive mechanism,
wherein, prior to performing the analysis, the controller performs the steps of: obtaining information about the type of the sample holder, determining the appropriate one of the plurality of analysis positions on the basis of the obtained information about the type of the sample holder, and controlling the drive mechanism to move the detector into the determined analysis position.

2. The charged particle beam system as set forth in claim 1, wherein said sample holder is connected with said controller via plural signal lines, and wherein the controller obtains the information about the type of the sample holder on the basis of the state of electrical connection between the plural signal lines.

3. The charged particle beam system as set forth in claim 1, wherein said sample holder has an information storage section in which there is stored information about the type of the sample holder, and wherein said controller obtains the information about the type of the sample holder by reading this information about the type of the sample holder from the information storage section.

4. The charged particle beam system as set forth in claim 1, further comprising a manual control unit permitting a user to enter information about the type of said sample holder, and wherein said controller obtains the information about the type of the sample holder on the basis of the information about the type of the sample holder entered via the manual control unit.

5. The charged particle beam system as set forth in claim 1,
wherein there is further included an objective lens,
wherein said controller performs the step of obtaining information about the type of the objective lens, and
wherein during the step of determining said analysis position, the controller determines the appropriate analysis position on the basis of both the information about the type of the sample holder and the information about the type of the objective lens.

* * * * *

UNITED STATES PATENT AND TRADEMARK OFFICE
CERTIFICATE OF CORRECTION

PATENT NO. : 10,529,530 B2
APPLICATION NO. : 15/341309
DATED : January 7, 2020
INVENTOR(S) : Shuji Kawai Page 1 of 1

It is certified that error appears in the above-identified patent and that said Letters Patent is hereby corrected as shown below:

In the Claims

Column 14, Line 21, Claim 1, delete first occurrence "the" and insert -- an --

Signed and Sealed this
Fifth Day of May, 2020

Andrei Iancu
*Director of the United States Patent and Trademark Office*